United States Patent
Andersson et al.

(10) Patent No.: US 8,171,776 B2
(45) Date of Patent: May 8, 2012

(54) PHASE CONTROLLER FOR A DUAL MOTOR TORQUE DETECTING DEVICE

(75) Inventors: Niclas Andersson, Karlstad (SE); Joakim Kullander, Säffle (SE); Peter Lundberg, Åmål (SE); Peter Adrian, Arvika (SE)

(73) Assignee: BTG Pulp & Paper Sensors AB, Säffle (SE)

( * ) Notice: Subject to any disclaimer, the term of this patent is extended or adjusted under 35 U.S.C. 154(b) by 419 days.

(21) Appl. No.: 12/523,076

(22) PCT Filed: Dec. 19, 2007

(86) PCT No.: PCT/SE2007/051036
§ 371 (c)(1),
(2), (4) Date: Jul. 31, 2009

(87) PCT Pub. No.: WO2008/088265
PCT Pub. Date: Jul. 24, 2008

(65) Prior Publication Data
US 2010/0162799 A1  Jul. 1, 2010

(30) Foreign Application Priority Data
Jan. 16, 2007  (SE) .................................. 0700085

(51) Int. Cl.
*G01N 11/14* (2006.01)
(52) U.S. Cl. ...................... 73/54.28; 73/54.01; 73/54.02; 73/54.31; 318/432; 318/433; 318/608

(58) Field of Classification Search ................. 73/53.01, 73/54.01–54.43; 318/3, 8, 432, 608, 671, 318/683
See application file for complete search history.

(56) References Cited

U.S. PATENT DOCUMENTS

| | | | | |
|---|---|---|---|---|
| 3,751,975 A | * | 8/1973 | Katsura | 73/54.38 |
| 4,373,147 A | * | 2/1983 | Carlson, Jr. | 318/48 |
| 4,375,047 A | | 2/1983 | Nelson et al. | |
| 4,862,735 A | * | 9/1989 | Williams et al. | 73/54.24 |
| 5,600,058 A | * | 2/1997 | Preikschat et al. | 73/54.32 |
| 5,684,247 A | * | 11/1997 | Preikschat | 73/54.32 |
| 7,456,538 B2 | * | 11/2008 | Nai et al. | 310/114 |

FOREIGN PATENT DOCUMENTS

| | | |
|---|---|---|
| WO | WO 2005/026697 A1 | 3/2005 |
| WO | WO 2005/057059 A1 | 6/2005 |
| WO | WO 2005/057153 A1 | 6/2005 |

* cited by examiner

*Primary Examiner* — David Rogers
(74) *Attorney, Agent, or Firm* — Dickstein Shapiro LLP

(57) ABSTRACT

A torque measuring device for determining properties such as viscosity, shearing force or concentration in liquids or suspensions. The device comprises two elastically connected concentric axles in the form of one external hollow axle through which an inner measuring axle extends, and an element responsive to the measured medium located on a distal end of the measuring axle. The axles are individually propelled by electrical motors. The motors are operated such that the axles rotate at generally constant speed and, simultaneously, the phase between the two are controlled irrespective of applied speed and torque. The torque is measured through the degree of load of the motor propelling the inner axle, which is provided as an output signal.

5 Claims, 1 Drawing Sheet

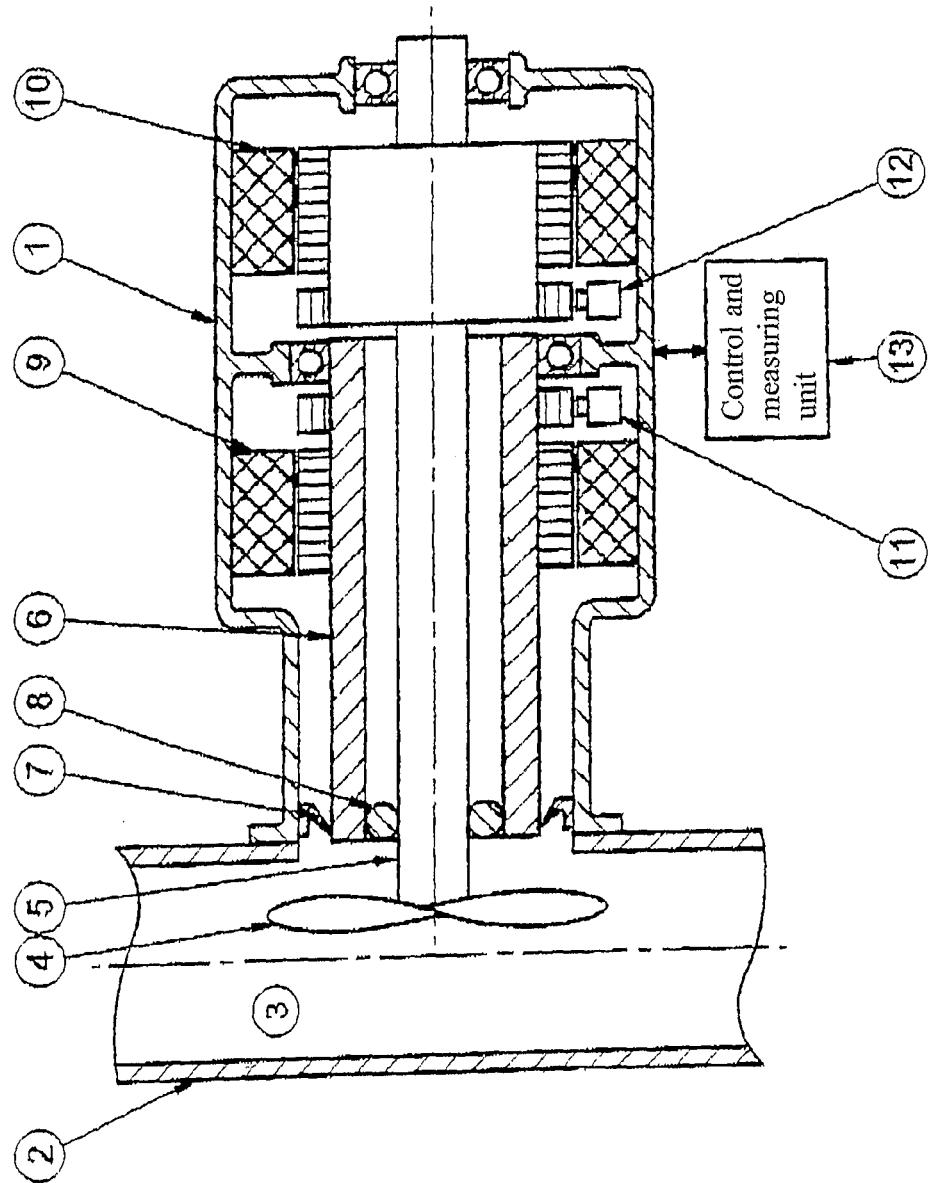

PHASE CONTROLLER FOR A DUAL MOTOR TORQUE DETECTING DEVICE

The present invention relates to a device for, or more specifically, a principle for torque measuring devices or gauges, for measurement of for example pulp concentration, viscosity, dryness and rheological characteristics, which operates in accordance with the principle of force balance.

BACKGROUND OF THE INVENTION

Revolving measuring devices for concentration, shearing force, viscosity, dryness, rheological characteristics etc. have been in use for a long time in the process industry. The measuring devices are engineered after well established principles that in some cases date back to the 1960's. The fundamental principle is that a probe is rotated in a medium and the resistance torque that arise at the probe or sensor, as it is frequently called, is measured and transformed into a suitable out signal.

The most frequently occurring design is the principle with a dual axle system which measures the angular difference between two concentric axles, wherein the outer hollow axle is propelled with a constant rotational speed and the inner measuring axle is elastically connected to the hollow axle. The elastic connection also serves as sealing against the process medium. The probe is fixedly attached to the part of the measuring axle situated in the medium. The dual axle principle eliminates problems with additional torque, in the form of friction from the sealing and the bearing of the measuring axle, which could affect the measuring result, since this friction might vary. Said method is in control engineering usually referred to as the principle of motion balance. Disadvantages that occur with such a system are that temperature, pressure, and ageing of the material negatively affects the characteristics of the system, since the elastic sealing between the hollow axle and the measuring axle is allowed to operate outside of its zero position. Another characteristic that is negatively affected is the linearity of the system.

However, if the axle arrangement is equipped with a feedback system, which restores the inner axle to its zero position regardless of the size of the arisen torque and measures the force required, the effect of said disturbing factors are to a large extent eliminated and the result will be a more linear and long term stable measuring system. Such a feedback system is said to operate in accordance with the principle of balance of forces. Today, the most common way to apply feedback to a system for torque measuring device is through an electromagnetic feedback system, wherein the current required to retain the measuring axle in its zero position is measured.

Even though feedback systems are not novel in the area of torque measuring devices and even though they continuously have evolved since the 60's there are some existing disadvantages that remain hard, not to say impossible to eliminate with currently available technology. The use of electromagnetic systems always result in some remanence, which in turn result in a measurement error. Considerable improvements have been made with regard to this the last couple of years, but it is in the nature of the subject that obtaining zero remanence is impossible using available technology. Furthermore, said continuous development has not notably reduced the complexity and price of the measuring devices and even if the total weight has been reduced it is desirable that the weight is further reduced. The linearity has been improved, but also here one is dependent of the magnetization curve of the iron in use, which results in some nonlinearity.

In today's process industry, with high demands on quality and equally high volumes of production, one is in many measurement positions completely dependent on measuring devices with high accuracy. Unfortunately measuring devices which do not comply with these demands are sometimes selected. The reasons for this can be many, for example high prices, high weights and large complexity of the measuring devices with high accuracy. Hence there is a lot to gain if the measuring devices can be further improved at the same time as the accuracy is increased, the weight is reduced and the prices is, if not lowered so at least kept on the same level.

BRIEF SUMMARY OF THE INVENTION

One object of the present invention is to increase the accuracy and the linearity. Additional objects are to reduce the complexity and weight, and through that obtain a system that is more energy efficient, more compact and with increased user friendliness.

The present invention implies that the axles, in comparison to previous feedback systems where only the outer axle is propelled and the feedback system connected to the inner axle is dependant on the rotation of the outer axle, instead are propelled independently of each other with individual electrical motors each with the same rotational speed in a way so that the phase between them is controlled. The preferred phase is the phase which corresponds to the zero position between the axles i.e. the phase in which no torque is being transferred through the elastic sealing, however it is also possible to select a different phase which is constant or varying in a controlled manner and to filter the signal. By using a type of motor such as permanent magnet synchronous motor for propulsion of at least the inner axle, the measuring axle, a direct measurement of the torque is obtained through the relation between current to the motor and the torque delivered from the motor. This type of motor can also be placed surrounding the hollow axle for propulsion of same, which eliminates the need of transmission with gear, which contributes to low weight. Furthermore motors of the type permanent magnet synchronous motor eliminates problems with remanence and improves the linearity at the same time as the rotational speed easily can be adapted to the present application and it gives the ability to control the rotational speed and/or the phase also through braking. It can also be reversed in case of an object, e.g. a piece of a plastic bag, gets stuck on the probe, to possibly get this object to fall off. The energy efficient and compact design also provides for high efficiency and lower costs of installation through the invention.

BRIEF DESCRIPTION OF THE DRAWINGS

The sole drawing shows the torque measuring device of the present invention.

DETAILED DESCRIPTION OF THE INVENTION

The present invention is described in greater detail below with assistance of a preferred embodiment under referral to the enclosed drawing.

In the drawing a schematic cross section through a torque measuring device 1 is shown, which is mounted on a process pipe 2 in which a measurement medium 3 flows passing a probe 4. Said probe 4 is fixedly attached to a measuring axle 5 in a dual axle system, which apart from the measuring axle 5 also comprises a hollow axle 6, which seals off the torque measuring device 1 from the measured medium 3 by means of a sealing 7. An elastic connection 8 between the hollow axle 6 and the measuring axle 5 permits the two axles 5, 6 to have a relative angular displacement at a change in the torque that the medium 3 exert on the probe 4.

The two axles 5, 6 is propelled independently by individual electrical motors 9, 10. The motor 9 propels the outer axle, i.e. the hollow axle 6, and the motor 10 propels the inner axle, i.e. the measuring axle 5. One of the motors 9 or 10 is controlled in order to keep a constant and for the application adapted rotational speed, while the other motor 9 or 10 is controlled so that the phase between the axles 5, 6 always remain the same, and corresponds to the zero position between the axles 5, 6, i.e. the position where no torque is transferred through the elastic sealing 8 between the axles 5, 6.

The phase between the two axles 5, 6 is detected by sensors 11 and 12. The shown example of an embodiment requires that at least the one of the electrical motors 10 is constructed in such a way that it shows a constant, or at least under present circumstances known, relationship between the torque and the degree of load applied on the measuring axle 5 by the probe 4 or the power consumption of the motor 10. The degree of load or power consumption is transformed to a, for the purpose, suitable out signal.

The invention claimed is:

1. A torque measuring device for determining properties such as viscosity, shearing force or concentration in liquids or suspensions, the device comprising: a) two elastically connected concentric axles in the form of one external hollow axle (6) through which an inner measuring axle (5) extends, b) an element (4) responsive to the measured medium (3) located, on a distal end of the measuring axle (5); and c) the axles (6, 5) are individually propelled by electrical motors (9, 10), said motors (9, 10) are operated such that the axles rotate at generally constant speed at the same time as the phase between the two are controlled irrespective of applied speed and torque, wherein the torque is measured through the degree of load of the motor (10) propelling the inner axle (5), which is provided as an output signal.

2. The device according to claim 1, wherein the degree of load for measuring torque is the power consumption of the motor (10) that rotates the measuring axles.

3. The device according to claim 1, further comprising a controller (13) adapted to operate the motor (10), such that it rotates the measuring axle (5) at a desired, generally constant, speed and to operate the motor (9), such that it rotates the outer axle (6) in order to maintain a desired constant phase relative to the measuring axle (5).

4. The device according to claim 1, further comprising a controller (13) adapted to operate the motor (9) such that it rotates the outer axle (6) at the desired, generally constant speed and to operate the motor (10), such that it rotates the measuring axle (5) in order to obtain a desired constant phase relative to the outer axle (6).

5. The device according to claim 1, wherein the desired phase corresponds to the position where no torque is transferable between the elastically connected axles (5, 6).

* * * * *